United States Patent
Kang

(10) Patent No.: US 11,314,525 B2
(45) Date of Patent: Apr. 26, 2022

(54) METHOD FOR UTILIZING GENETIC INFORMATION AND ELECTRONIC DEVICE THEREOF

(71) Applicant: Samsung Electronics Co., Ltd., Suwon-si (KR)

(72) Inventor: Kiman Kang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 128 days.

(21) Appl. No.: 16/724,091

(22) Filed: Dec. 20, 2019

(65) Prior Publication Data

US 2020/0201657 A1 Jun. 25, 2020

(30) Foreign Application Priority Data

Dec. 20, 2018 (KR) .................. 10-2018-0165947

(51) Int. Cl.
*G06F 9/445* (2018.01)
*G16B 20/00* (2019.01)

(52) U.S. Cl.
CPC ......... *G06F 9/44505* (2013.01); *G16B 20/00* (2019.02)

(58) Field of Classification Search
CPC ...... G06F 9/44505; G06F 3/011; G06F 3/005; G16B 20/00
See application file for complete search history.

(56) References Cited

U.S. PATENT DOCUMENTS

| | | | | |
|---|---|---|---|---|
| 7,124,375 B1* | 10/2006 | Steele | .................... | G09G 5/024 |
| | | | | 715/865 |
| 2010/0271507 A1* | 10/2010 | Hung | ................. | H04N 5/23219 |
| | | | | 348/231.99 |
| 2012/0329561 A1* | 12/2012 | Evans | ..................... | A63F 13/79 |
| | | | | 463/43 |
| 2013/0325493 A1* | 12/2013 | Wong | ..................... | G16H 50/20 |
| | | | | 705/2 |
| 2014/0358012 A1* | 12/2014 | Richards | .............. | A61B 5/6802 |
| | | | | 600/479 |
| 2015/0323511 A1 | 11/2015 | Hendry et al. | | |
| 2016/0321395 A1 | 11/2016 | Colby et al. | | |
| 2017/0080346 A1* | 3/2017 | Abbas | ..................... | A63F 13/79 |
| 2018/0096198 A1* | 4/2018 | Tzvieli | ..................... | H04N 5/33 |
| 2018/0317854 A1* | 11/2018 | Chao | .................... | A61B 5/7221 |
| 2019/0110755 A1* | 4/2019 | Capodilupo | ........ | G06K 9/6282 |
| 2019/0246895 A1* | 8/2019 | Kodimer | ................ | G06T 5/009 |
| 2019/0362531 A1* | 11/2019 | Smith | .................... | G16B 45/00 |
| 2020/0234499 A1* | 7/2020 | Hwang | ................ | H04N 21/434 |

* cited by examiner

*Primary Examiner* — Jaweed A Abbaszadeh
*Assistant Examiner* — Cheri L Harrington

(57) ABSTRACT

A method of operating an electronic device according to various embodiments r may include executing an application, identifying at least one genetic element corresponding to an attribute related to genetic information of a user with respect to the application, determining a setting value for the attribute based on the at least one genetic element, and providing a service related to the application based on the determined setting value.

22 Claims, 11 Drawing Sheets

METHOD FOR UTILIZING GENETIC INFORMATION AND ELECTRONIC DEVICE THEREOF

CROSS REFERENCE TO RELATED APPLICATION

This application is based on and claims priority under 35 U.S.C. 119 to Korean Patent Application No, 10-2018-0165947, filed on Dec. 20, 2018, in the Korean Intellectual Property Office, the disclosures of which are herein incorporated by reference in their entireties.

BACKGROUND

1. Field

Various embodiments described below relate to a method for utilizing genetic information, and an electronic device thereof.

2. Description of Related Art

With the development of technologies, an electronic device utilizing genetic information has come into wide use. For example, there is an electronic device for providing a service related to an application by utilizing the genetic information.

SUMMARY

Various embodiments may provide a method for utilizing genetic information, and an electronic device thereof.

Various embodiments may provide a method for determining a setting value for an attribute of application based on a genetic element of a user, and an electronic device thereof.

Various embodiments may provide a method for determining a setting value for a Red, Green, Blue (RGB) configuration of image data based on a gene related to color blindness of a user, and an electronic device thereof.

Various embodiments may provide a method for determining a setting value for a shape of an avatar based on a gene related to an appearance of a user, and an electronic device thereof.

Various embodiments may provide a method for determining a setting value for a sensor (e.g., a PhotoPlethysmoGraphy (PPG) sensor, an Infra-Red (IR) sensor) on the basis a gene related to a user's heart condition or iris color, and an electronic device thereof.

Technical problems to be achieved in the disclosure are not limited to the technical problems mentioned above, and other technical problems not mentioned herein can be clearly understood by those skilled in the art to which the disclosure pertains from the following descriptions.

A method of operating an electronic device according to various embodiments may include identifying at least one genetic element corresponding to an attribute related to genetic information of a user with respect to the application, determining a setting value for the attribute, based on the at least one genetic element, and providing a service related to the application, based on the determined setting value.

An electronic device according to various embodiments may include a camera, a display, a sensor, a memory, a transceiver, and a processor. The processor may be configured to execute an application, identify at least one genetic element corresponding to an attribute related to genetic information of a user with respect to the application, determine a setting value for the attribute, based on the at least one genetic element, and provide a service related to the application, based on the determined setting value.

A method for utilizing genetic information and an electronic device thereof according to various embodiments may determine a setting value for an attribute of application based on a genetic element of a user, thereby providing an individualized user experience and an improved application service.

Advantages acquired in the disclosure are not limited to the aforementioned advantages, and other advantages not mentioned herein can be clearly understood by those skilled in the art to which the disclosure pertains from the following descriptions.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document. Those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
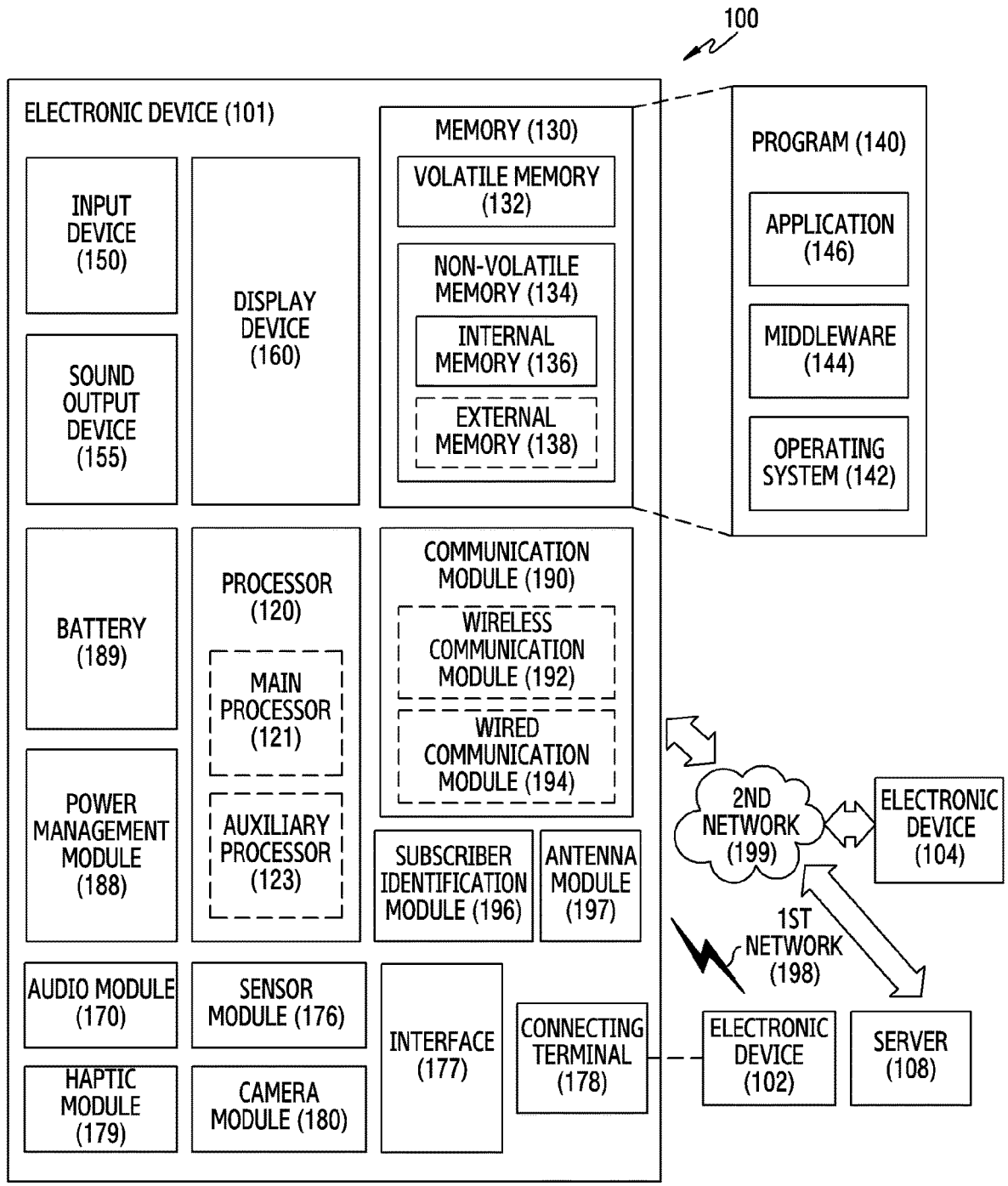
FIG. 1 is a block diagram illustrating an electronic device in a network environment according to various embodiments.

FIG. 1 is a block diagram illustrating an electronic device (101) in a network environment (100) according to various embodiments. Referring to FIG. 1, the electronic device (101) in the network environment (100) may communicate with an electronic device (102) via a first network (198) (e.g., a short-range wireless communication network), or an electronic device (104) or a server (108) via a second network (199) (e.g., a long-range wireless communication network). According to an embodiment, the electronic device (101) may communicate with the electronic device (104) via the server (108). According to an embodiment, the electronic device (101) may include a processor (120), memory 130), an input device (150), a sound output device (155), a display device (160), an audio module (170), a sensor module (176), an interface (177), a haptic module (179), a camera module (180), a power management module (188), a battery (189), a communication module (190), a subscriber identification module (SIM) (196), or an antenna module (197). In some embodiments, at least one (e.g., the display device (160) or the camera module (180)) of the components may be omitted from the electronic device (101), or one or more other components may be added in the electronic device (101). In some embodiments, some of the components may be implemented as single integrated circuitry. For example, the sensor module (176) (e.g., a fingerprint sensor, an iris sensor, or an illuminance sensor) may be implemented as embedded in the display device (160) (e.g., a display).

The processor (120) may execute, for example, software a program (140)) to control at least one other component (e.g., a hardware or software component) of the electronic device (101) coupled with the processor (120), and may perform various data processing or computation. According to one embodiment, as at least part of the data processing or computation, the processor (120) may load a command or data received from another component (e.g., the sensor module (176) or the communication module (190)) in volatile memory (132), process the command or the data stored in the volatile memory (132), and store resulting data in non-volatile memory (134). According to an embodiment, the processor (120) may include a main processor (121) (e.g., a central processing unit (CPU) or an application processor (AP)), and an auxiliary processor (123) (e.g., a graphics processing unit (GPU), an image signal processor (ISP), a sensor hub processor, or a communication processor (CP)) that is operable independently from, or in conjunction with, the main processor (121). Additionally or alternatively, the auxiliary processor (123) may be adapted to consume less power than the main processor (121), or to be specific to a specified function. The auxiliary processor (123) may be implemented as separate from, or as part of the main processor (121.

The auxiliary processor (123) may control at least some of functions or states related to at least one component (e.g., the display device (160), the sensor module (176), or the communication module (190)) among the components of the electronic device (101), instead of the main processor (121) while the main processor (121) is in an inactive (e.g., sleep) state, or together with the main processor (121) while the main processor (121) is in an active state (e.g., executing an application). According to an embodiment, the auxiliary processor (123) (e.g., an image signal processor or a communication processor) may be implemented as part of another component (e.g., the camera module (180) or the communication module (190)) functionally related to the auxiliary processor (123).

The memory (130) may store various data used by at least one component (e.g., the processor (120) or the sensor module (176)) of the electronic device (101). The various data may include, for example, software (e.g., the program (140)) and input data or output data for a command related thereto. The memory (130) may include the volatile memory (132) or the non-volatile memory (134).

The program (140) may be stored in the memory (130) as software, and may include, for example, an operating system (OS) (142), middleware (144), or an application (146).

The input device (150) may receive a command or data to be used by other component (e.g., the processor (120)) of the electronic device (101), from the outside e.g., a user) of the electronic device (101). The input device (150) may include, for example, a microphone, a mouse, a keyboard, or a digital pen (e.g., a stylus pen).

The sound output device (155) may output sound signals to the outside of the electronic device (101). The sound output device (155) may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device (160) may visually provide information to the outside (e.g., a user) of the electronic device (101). The display device (160) may include, for example, a display, a hologram device, or a projector and control circuitry to control a corresponding one of the display, hologram device, and projector. According to an embodiment, the display device (160) may include touch circuitry adapted to detect a touch, or sensor circuitry (e.g., a pressure sensor) adapted to measure the intensity of force incurred by the touch.

The audio module (170) may convert a sound into an electrical signal and vice versa. According to an embodiment, the audio module (170) may obtain the sound via the input device (150), or output the sound via the sound output device (155) or a headphone of an external electronic device (e.g., an electronic device (102)) directly (e.g., wiredly) or wirelessly coupled with the electronic device (101).

The sensor module (176) may detect an operational state (power or temperature) of the electronic device (101) or an environmental state (e.g., a state of a user) external to the electronic device (101), and then generate an electrical signal or data value corresponding to the detected state. According to an embodiment, the sensor module (176) may include, for example, a gesture sensor, a gyro sensor, an atmospheric pressure sensor, a magnetic sensor, an acceleration sensor, a grip sensor, a proximity sensor, a color sensor, an infrared (TR) sensor, a biometric sensor, a temperature sensor, a humidity sensor, or an illuminance sensor.

The interface (177) may support one or more specified protocols to be used for the electronic device (101) to be coupled with the external electronic device (e.g., the electronic device (102)) directly (e.g., wiredly) or wirelessly. According to an embodiment, the interface (177) may include, for example, a high definition multimedia interface (HDMI), a universal serial bus (USB) interface, a secure digital (SD) card interface, or an audio interface.

A connecting terminal (178) may include a connector via which the electronic device (101) may be physically connected with the external electronic device the electronic device (102)). According to an embodiment, the connecting terminal (178) may include, for example, a HDMI connector, a USB connector, a SD card connector, or an audio connector (e.g., a headphone connector).

The haptic module (179) may convert an electrical signal into a mechanical stimulus (e.g., a vibration or a movement) or electrical stimulus which may be recognized by a user via his tactile sensation or kinesthetic sensation. According to an embodiment, the haptic module (179) may include, for example, a motor, a piezoelectric element, or an electric stimulator.

The camera module (180) may capture a still image or moving images. According to an embodiment, the camera module (180) may include one or more lenses, image sensors, image signal processors, or flashes.

The power management module (188) may manage power supplied to the electronic device (101). According to one embodiment, the power management module (188) may be implemented as at least part of, for example, a power management integrated circuit (PMIC).

The battery (189) may supply power to at least one component of the electronic device (101). According to an embodiment, the battery (189) may include, for example, a primary cell which is not rechargeable, a secondary cell which is rechargeable, or a fuel cell.

The communication module (190) may support establishing a direct (e.g., wired) communication channel or a wireless communication channel between the electronic device (101) and the external electronic device (e.g., the electronic device (102), the electronic device (104), or the server (108)) and performing communication via the established communication channel. The communication module (190) may include one or more communication processors that are operable independently from the processor (120) (e.g., the application processor (AP)) and supports a direct (e.g., wired) communication or a wireless communication. According to an embodiment, the communication module (190) may include a wireless communication module (192) (e.g., a cellular communication module, a short-range wireless communication module, or a global navigation satellite system (GNSS) communication module) or a wired communication module (194) (e.g., a local area network (LAN) communication module or a power line communication (PLC) module). A corresponding one of these communication modules may communicate with the external electronic device via the first network (198) (e.g., a short-range communication network, such as Bluetooth™, wireless-fidelity (Wi-Fi) direct, or infrared data association (IrDA)) or the second network (199) (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module (192) may identify and authenticate the electronic device (101) in a communication network, such as the first network (198) or the second network (199), using subscriber information (e.g., international mobile subscriber identity (IMSD) stored in the subscriber identification module (196).

The antenna module (197) may transmit or receive a signal or power to or from the outside (e.g., the external electronic device) of the electronic device (101). According to an embodiment, the antenna module (197) may include a plurality of antennas. In such a case, at least one antenna appropriate for a communication scheme used in the communication network, such as the first network (198) or the second network (199), may be selected, for example, by the communication module (190) (e.g., the wireless communication module (192)) from the plurality of antennas. The signal or the power may then be transmitted or received between the communication module (190) and the external electronic device via the selected at least one antenna.

At least some of the above-described components may be coupled mutually and communicate signals (e.g., commands or data) therebetween via an inter-peripheral communication scheme (e.g., a bus, general purpose input and output (GPM), serial peripheral interface (SPI), or mobile industry processor interface (MIPI)).

According to an embodiment, commands or data may be transmitted or received between the electronic device (101) and the external electronic device (104) via the server (108) coupled with the second network (199). Each of the electronic devices (102) and (104) may be a device of a same type as, or a different type, from the electronic device (101). According to an embodiment, all or some of operations to be executed at the electronic device (101) may be executed at one or more of the external electronic devices (102), (104), or (108). For example, if the electronic device (101) should perform a function or a service automatically, or in response to a request from a user or another device, the electronic device (101), instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device (101). The electronic device (101) may provide the outcome, with or without further processing of the outcome, as at least part of a reply to the request. To that end, a cloud computing, distributed computing, or client-server computing technology may be used, for example.

An electronic device (e.g., the electronic device 101) according to various embodiments may include a camera, a display, a sensor, a memory, a transceiver, and a processor. The processor may be configured to execute an application, identify at least one genetic element corresponding to an attribute related to genetic information of a user with respect to the application, determine a setting value for the attribute, based on the at least one genetic element, and provide a service related to the application, based on the determined setting value.

In various embodiments, the processor may be configured to transmit, to a server, information on the application by controlling the transceiver, and receive, from the server, information including the at least one genetic element determined based on the information on the application by controlling the transceiver.

In various embodiments, the processor may be configured to identify an attribute related to user's genetic information for the application, and identify the at least one genetic element corresponding to the attribute from the genetic information stored in the electronic device.

In various embodiments, the at least one genetic element corresponding to the attribute may be determined based on a table representing a mapping relation between attributes related to a plurality of applications and genetic elements of the genetic information.

In various embodiments, the processor may be configured to compare the setting value with a default setting value, represent a message for inquiring a setting value change if the setting value is different from the default setting value as a result of the comparison, receive a response to the message by controlling the transceiver, and adjust the default setting value to the setting value if the response to the message indicates the setting value change.

In various embodiments, the processor may be configured to maintain the default setting value for the attribute if the response to the message indicates to maintain the setting value, and transmit information on a genetic element related to the maintaining of the setting value to a server by controlling the transceiver. The information on the genetic element may be used to update user's condition information related to the genetic element.

In various embodiments, the processor may be configured to store the setting value for the attribute in the memory, and provide the service related to the application based on the stored setting value without identifying the at least one genetic element in response to re-execution of the application.

In various embodiments, the at least one genetic element may include a gene related to color blindness, and the attribute includes a Red, Blue, Green (RGB) configuration for image data. The processor may be configured to detect the color blindness of the user based on the gene related to the color blindness, adjust an RGB value for the RGB configuration to a Yellow, Blue, Maintained (YBM) value, based on the detection of the color blindness, and display the image data, based on the YBM value.

In various embodiments, the at least one genetic element may include at least one of a gene related to a race of the user, a gene related to a gender of the user, a gene related to a height of the user, a gene related to hair color of the user, a gene related to eye color of the user, a gene related to skin color of the user, and a gene related to a contour of the user. The attribute may include a shape of an avatar. The processor may be configured to obtain one or more images including an external object by using a camera, determine the shape of the avatar corresponding to the external object, based on the at least one genetic element, create the avatar, based on the shape of the avatar, and display the avatar via a display.

In various embodiments, the at least one genetic element may include at least one of a gene related to a race of the user, a gene related to hair color of the user, a gene related to eye color of the user, and a gene related to skin color of the user. The attribute may include a camera configuration. The processor may be configured to obtain one or more images including an external object by using a camera of which a shutter speed is adjusted based on the at least one genetic element, create an avatar corresponding to the external object, and display the avatar via a display.

In various embodiments, the at least one genetic element may include at least one of a gene related to skin color of the user and a gene related to a heart condition of the user. The attribute may include a configuration for a PhotoPlethysmoGraphy (PPG) sensor. The processor may be configured to measure a bio-signal of the user, based on a default setting value of the PPG sensor, determine whether an intensity of the bio-signal is within a measurement range, and if the intensity of the bio-signal is out of the measurement range, adjust at least one of a current value of a light emitter of the PPG sensor and a Signal to Noise Ratio (SNR) threshold of the PPG sensor, based on the at least one genetic element.

In various embodiments, the at least one genetic element may include a gene related to iris color of the user. The attribute may include a configuration for an Infra-Red (IR) sensor. The processor may be configured to obtain an iris signal of the user, based on a default setting value of the IR sensor, determine whether the iris signal is received to be greater than or equal to a criterion, and if the iris signal is not received to be greater than or equal to the criterion, adjust at least one of a wavelength of a signal of a light emitter of the IR sensor, a frequency band of a signal of the light emitter, and a resolution of an image sensor of a light receiver of the IR sensor.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A, and B," "at least one of A or B," "A B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program (140)) including one or more instructions that are stored in a storage medium (e.g., internal memory (136) or external memory (138)) that is readable by a machine (e.g., the electronic device (101)). For example, a processor (e.g., the processor (120)) of the machine (e.g., the electronic device (101)) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Terms used in the disclosure are defined as follows.

'Genetic information' implies a user's biological characteristic determined by a gene. The genetic information may include at least one genetic element. In various embodiments, the 'genetic information' may also be referred to as 'gene information'.

The 'genetic element' implies an individual element constituting genetic information. For example, the genetic element may include at least one of a gene related to color blindness, a gene related to a race of a user of an electronic device (e.g., the electronic device 101), a gene related to a user's gender, a gene related to a user's height, a gene related to user's hair color, a gene related to user's eye color (e.g., iris color), a gene related to user's skin color, a gene related to a user's contour, and a gene related to a user's heart condition. The aforementioned genetic elements are for illustrative purposes only, and thus the genetic elements that can be included in the genetic information are not limited to the aforementioned examples.

An 'attribute of application' implies an attribute related to the user's genetic information for the application. In various embodiments, the attribute of application may also be referred to as attribute information of the application or configuration information of the application, and may also be simply referred to as 'attribute' or 'configuration'. The attribute of application implies an attribute or configuration in which a setting value change is required depending on the genetic information for the application. For example, the attribute of application may include at least one of an RGB configuration for image data, a shape of an avatar, a camera configuration, a configuration for a PPG sensor, and a configuration for an IR sensor. According to various embodiments, at least one attribute may be defined for each individual application, and at least one attribute may correspond to at least one genetic element. According to various embodiments, one attribute may correspond to one genetic element. For another example, one attribute may correspond to two or more genetic elements. For another example, a plurality of attributes may correspond to one genetic element.

A 'setting value for the attribute of application' implies a value related to a configuration applied to provide a service through the application. For example, a setting value for the RGB configuration may include at least one of an RGB value and YBM value of image data. For another example, a setting value for a shape of an avatar may include at least one of a size of the avatar (e.g., a height or body shape of the avatar), eye color of the avatar, skin color of the avatar, a race of the avatar, a gender of the avatar, and a contour of the avatar. For another example, a setting value for the configuration of the PPG sensor may include at least one of a current value of a light emitter of the PPG sensor and a Signal to Noise Ratio (SNR) threshold of the PPG sensor. For another example, a setting value for the configuration of the IR sensor may include at least one of a current value of a light emitter of the IR sensor and an SNR threshold of the IR sensor. For another example, the setting value for the configuration of the IR sensor may include at least one of a wavelength (or a frequency band) of a signal of the light emitter of the IR sensor and a resolution of an image sensor of a light receiver of the IR sensor. According to various embodiments, at least one of setting values for respective attributes may be a default setting value for the attribute.

The 'avatar' implies an object in a virtual space corresponding to an external object included in one or more images obtained by using a camera (e.g., the camera module 180). The avatar may move in response to a motion of the external object detected by the camera module 180 and/or the sensor module 176.

A setting value for an electronic device (e.g., the electronic device 101) may be configured to be the same as that of another electronic device by considering a general user as to an individualized device for a specific individual other than a device shared with a plurality of users (hereinafter, referred to a public device) (e.g., a TeleVision (TV), a refrigerator). For example, a setting value that can be used in the individualized device may also be a common setting value for other individualized devices, such as an RGB value of a display, i.e., an LCD or OLED display, and a setting value of a photo diode (which measures a blood flow rate using photons penetrating or reflected from skin) for measuring a heartrate in a wearable device. It may be difficult to reflect a personal characteristic when using such a common setting value. For example, in case of an individualized service for creating an avatar, user-related data that can be obtained to create the avatar may be limited to image data through capturing, and a variety of variables may be applied according to a capturing condition. Therefore, the created avatar may not properly reflect an actual user.

Accordingly, various embodiments may provide a method and electronic device for utilizing genetic information.

Various embodiments may provide a method and electronic device for initially configuring or adjusting setting values of an individualized device to conform to a user's genetic characteristic by utilizing genetic information of the user.

Various embodiments may provide a method and electronic device for adjusting a RGB value of a suitable LCD and/or OLED display by considering color vision deficiency for a user who has inherited color vision deficiency (e.g., color blindness, color weakness).

Various embodiments may provide a method and electronic device for configuring signal strength of a sensor of a wearable device and/or a sensor of the electronic device 101 based on a gene related to a user's race.

Various embodiments may provide a method and electronic device for creating an avatar by considering user's genetic data in addition to captured image data.

Figure 2:
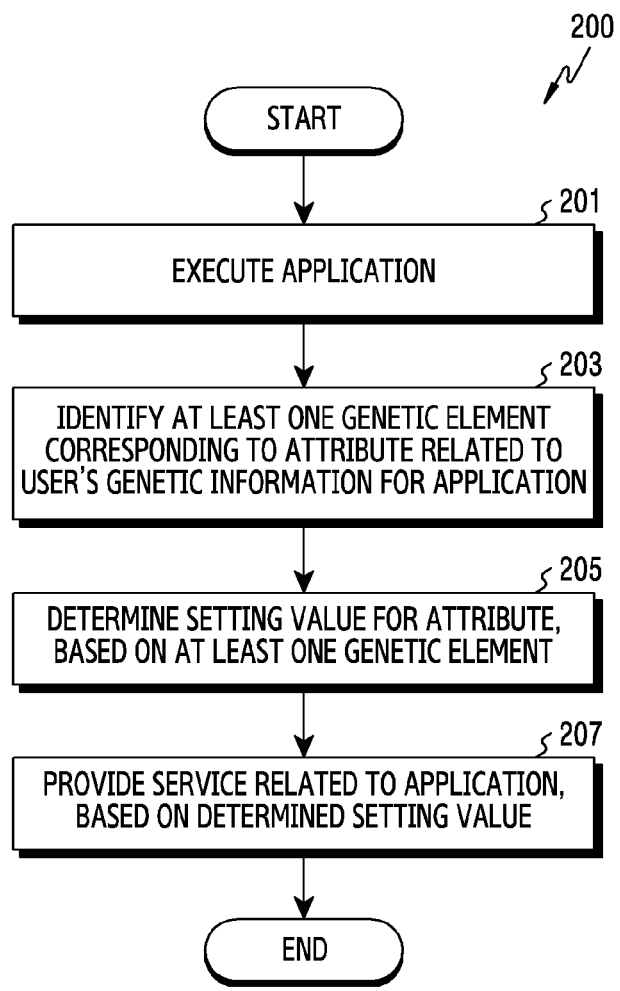
FIG. 2 illustrates an example of an operation of an electronic device according to various embodiments.

FIG. 2 illustrates an example of an operation of an electronic device according to various embodiments. Operations exemplified in a flowchart 200 of FIG. 2 may be performed by the electronic device 101 of FIG. 1 or by the processor 120 of the electronic device 101.

Referring to FIG. 2, in operation 201, the processor 120 may execute an application. For example, the processor 120 may execute an application selected according to a user's input from among at least one application installed in the electronic device 101. For example, the at least one application may include at least one of an application for which the display unit 160 is used or usable, an application for creating and/or representing an avatar (hereinafter, also referred to as an 'avatar application'), and an application for which an IR sensor (e.g., an iris scanner and/or an iris sensor) is used or usable.

In operation 203, the processor 120 may identify at least one genetic element corresponding to an attribute related to user's genetic information for the application. In other words, the processor 120 may identify the genetic information used for the application. In various embodiments, the at least one genetic element corresponding to the attribute of application may be determined based on attributes related to a plurality of applications and data representing a mapping relation between the genetic information and the genetic elements (hereinafter, also referred to as a genetic information mapping table). The genetic information mapping table may be stored in the memory 130 of the electronic device 101 and/or a memory of the server 108. At least one of the server 108, the electronic device 101, and the processor 120 of the electronic device 101 may determine at least one genetic element corresponding to the attribute of application, based on the genetic information mapping table.

In operation 205, the processor 120 may determine a setting value for the attribute, based on at least one genetic element. For example, the processor 120 may determine whether a setting value change is required for the attribute of application, based on the at least one genetic element. If a setting value identified as being suitable for the user according to the at least one genetic element is different from an initial setting value and/or a pre-set setting value, the processor 120 may determine that there is a request for changing the setting and may adjust the initial setting value and/or the pre-set setting value to a setting value suitable for the user. Regarding the setting value change, the processor 120 may consider user's feedback information for the setting value change.

In operation 207, the processor 120 may provide a service related to the application based on the determined setting value. The processor 120 may apply the determined setting value to the attribute of application, and may provide the service related to the application based on the setting value. For example, if the application is an application for which the display unit 160 is used or usable, an operation of providing the service related to the application may include an operation of displaying image data by using an RGB value or YBM value determined or adjusted according to a genetic element (e.g., a gene related to color blindness). For another example, if the application is an avatar application, an operation of providing the service related to the application may include an operation of creating and/or representing an avatar based on an avatar shape determined or adjusted according to a genetic element (e.g., a gene related to a race of a user, a gene related to a user's gender, a gene related to a user's height, a gene related to user's hair color, a gene related to user's eye color (e.g., iris color), a gene related to user's skin color, and/or a gene related to a user's contour). For another example, if the application is an application for which the PPG sensor is used or usable, an operation of providing a service related to an application may include an operation of measuring heartbeat information (e.g., a heartrate per minute, a heartbeat graph) based on a PPG sensor value (e.g., current of a light emitter, an SNR threshold) determined or adjusted according to a genetic element (e.g., a gene related to a user's heart condition and/or a gene related to user's skin color), and displaying a measurement result via the display unit 160. For another example, if the application is an application for which an IR sensor (e.g., an iris scanner and/or an iris sensor) is used or usable, an operation of providing a service related to an application may include an operation of measuring user's iris information based on an IR sensor value (e.g., current of a light emitter, an SNR threshold, a wavelength (or frequency band) of a signal of the light emitter, and/or a resolution of an image sensor of a light receiver of the IR sensor) determined or adjusted according to a genetic element (e.g., a gene related to user's eye color or iris color), and applying a measurement result.

According to various embodiments, the genetic information mapping table may be represented as shown in Table 1 below.

TABLE 1

| Attribute of application | Genetic element |
|---|---|
| RGB configuration | Gene related to color blindness |
| Shape of avatar | Gene related to user's race, gene related to user's gender, gene related to user's height, gene related to user's hair color, gene related to user's eye color (e.g., iris color), gene related to user's skin color, gene related to user's contour, and/or gene related to user's hair type (e.g., curl level or whether user's hair is curly) |
| Configuration for PPG sensor | Gene related to user's skin color |
| Configuration for IR sensor (e.g., iris scanner and/or iris sensor) | Gene related to user's eye color (e.g., iris color) |
| ... | ... |

In Table 1 above, an attribute and genetic element of an application described in the same row may correspond to each other. In addition, the attribute and genetic elements of the application described in Table 1 above are for illustrative purposes only, and various embodiments of the disclosure are not limited to the attribute and genetic elements of the application of Table 1.

For another example, the genetic information mapping table may further include additional information as shown in Table 2 below.

TABLE 2

| Application | Application category | Setting value | Genetic element | Feature |
|---|---|---|---|---|
| Healthcare application | Caffeine | Insight_1 | CYP1A2 | Caffeine sensitivity |
| Healthcare application | Walking | Pesplanus_1 | FBN1, CLNDBN | Flat foot |
| Display application | Color | Color_1 | CNGA3, CNGB3, GNAT2, OPN1LW, OPN1MW, OPN1SW | Color vision deficiency (color weakness) |

TABLE 2-continued

| Application | Application category | Setting value | Genetic element | Feature |
|---|---|---|---|---|
| Camera application | Avatar | SkinColor_1Frizzled_1 | FTO, CTB, CAN | Race, hair, skin, eye |
| Application related to IR sensor | Iris | Iris_color1 | EYCL1, EYCL2, EYCL3 | Iris color |
| ... | ... | ... | ... | ... |

In Table 2 above, an 'application category' implies information related to a genetic characteristic of a user among information that can be used in an application corresponding to the application category. In various embodiments, the term 'attribute of application' and the term 'application category' may be used interchangeably.

According to various embodiments, the processor 120 may configure a user avatar set based on user's genetic information in the avatar application. For example, the processor 120 may identify a genetic element (e.g., a hair curl gene, a skin color gene, an eye color gene, an ear shape gene, a chin shape gene, an eye size gene) corresponding to an attribute of the avatar application, and may configure the user avatar set based on the genetic element. In various embodiments, the user avatar set implies a set of available avatar shapes when user's genetic information is considered. The processor 120 may store the configured user avatar set in the memory 130. The processor 120 may combine a capture image for the user and the user avatar set in the avatar application to create an avatar similar to a user's actual shape. When only the capture image for the user is considered to create the avatar, the capture image may reflect a distorted user's shape according to surrounding illuminance and an angle of the camera module 180 with respect to the user. Therefore, an avatar which is not similar to the user's actual shape may be created. However, in various embodiments, the processor 120 may rapidly and similarly reflect the user's actual shape to the avatar by considering the user avatar set in addition to the capture image with respect to the user.

In various embodiments, the processor 120 may determine a setting value by considering user's genetic information for each tracker of a healthcare application (e.g., Samsung health). The healthcare application may include a plurality of trackers, and at least one attribute may be defined for each tracker. For example, the tracker of the healthcare application may include a heartbeat tracker, a blood pressure tracker, a diabetes tracker, a step (i.e., step count per unit time) tracker, a caffeine tracker, a food tracker, and an exercise tracker. The processor 120 may identify at least one genetic element corresponding to an attribute of each tracker (i.e., identify user's genetic information used for each tracker), and may determine a setting value for the attribute of the tracker. For example, the processor 120 may identify a gene related to heartbeat strength for the heartbeat tracker (i.e., whether the heartbeat is strong or weak), and may increase a current value of a light emitter of a PPG sensor based on a gene indicating that the heartbeat is weak. For another example, the processor 120 may identify a gene related to heartbeat information for the exercise tracker and/or a gene related, whether a weight training workout is effective, and may configure an event for the weight training workout, not an aerobic exercise, as a default event in the exercise tracker based on such a gene.

According to various embodiments, before at least one genetic element is identified in operation 203, the processor 120 may determine whether user profile information is within a margin of error. In various embodiments, the 'user profile information' implies information obtained or measured from the user to provide an application service, and may include, for example, at least one of a capture image for the user, heartbeat information for the user (e.g., a heartrate per minute, a heartbeat graph), and iris information. If it is determined that the user profile information is out of the margin of error, the processor 120 may determine to consider genetic information of the user, and may perform operations 203 to 207.

Figure 3:
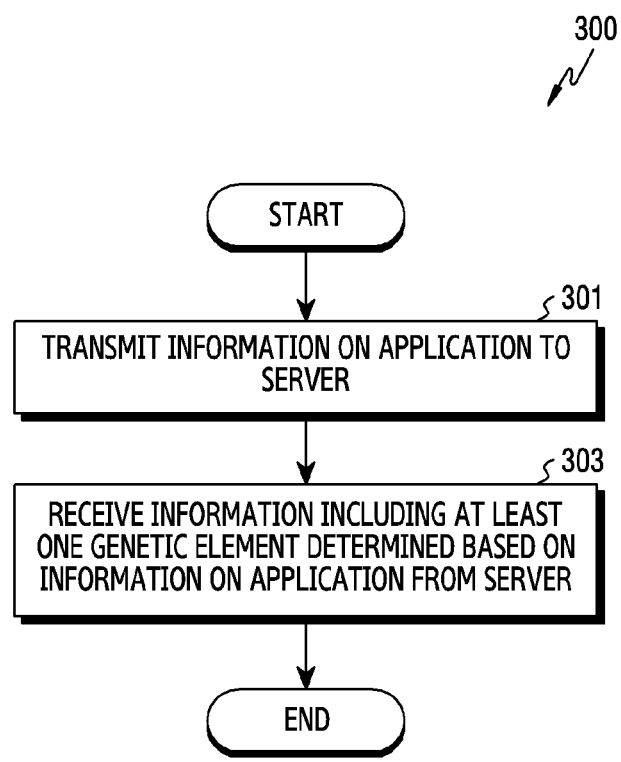
FIG. 3 illustrates an example of an operation of an electronic device for obtaining a genetic element from a server according to various embodiments.
Figure 4:
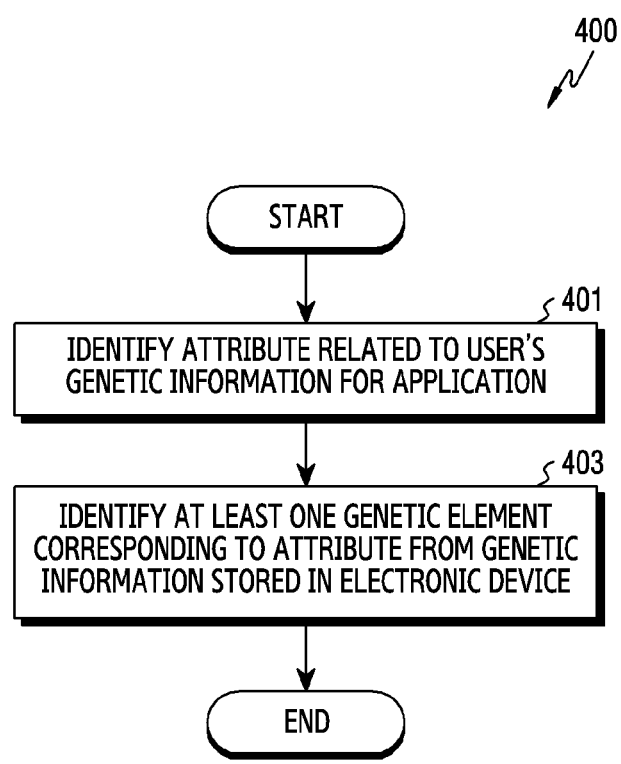
FIG. 4 illustrates an example of an operation of an electronic device for identifying a genetic element corresponding to an attribute of application from genetic information stored in the electronic device according to various embodiments.

Hereinafter, an operation in which the processor 120 identifies the genetic element will be described in greater detail with reference to FIG. 3 and FIG. 4, FIG. 3 illustrates an example of an operation of an electronic device for obtaining a genetic element from a server according to various embodiments. Operations exemplified in a flowchart 300 of FIG. 3 may be performed by the electronic device 101 of FIG. 1 or by the processor 120 of the electronic device 101.

Operations 301 to 303 of FIG. 3 may be related to the operation 203 of FIG. 2.

Referring to FIG. 3, in operation 301, the processor 120 may control the communication module 190 to transmit information on an application to the server 108. In various embodiments, user's genetic information may be stored in the server 108. In this case, the electronic device 101 may transmit the information on the application to the server 108, in order to obtain a genetic element from the server 108. In various embodiments, the information on the application may include at least one of an application IDentifier (ID), an application category, and/or an attribute of application. For example, the processor 120 may control the communication module 190 to transmit information including the application ID to the server 108. For another example, the processor 120 may determine the application category and/or the attribute of application based on the application ID, and may transmit information including the application category and/or the attribute of application to the server 108.

In operation 303, the processor 120 may control the communication module 190 to receive information including at least one genetic element determined based on the information on the application. In various embodiments, the server 108 may determine the application category and/or the attribute of application based on the application ID included in the information on the application, and may determine at least one genetic element corresponding to the application category and/or the attribute of application from genetic information stored in the server 108. The server 108 may transmit information including the determined at least one genetic element to the electronic device 101, and the processor 120 may control the communication module 190 to receive the information. For another example, the server 108 may identify the application category and/or attribute of application included in the information on the application, and may determine at least one genetic element corresponding to the application category and/or attribute of application from the genetic information stored in the server 108. The server 108 may transmit information including the determined at least one genetic element to the electronic device 101, and the processor 120 may control the communication module 190 to receive the information. In various embodiments, a genetic information mapping table may be stored in the server 108.

According to various embodiments, at least one account may be configured for the electronic device 101, and at least one account may correspond to user's genetic information. For another example, a plurality of accounts may be configured for the electronic device 101, at least one first account among the plurality of accounts may correspond to genetic information of a specific user, and at least one second account among the plurality of accounts may correspond to genetic information of another user. In various embodiments, the processor 120 may control the communication module 190 to transmit information indicating at least one account (hereinafter, referred to as "account information") to the server 108. The account information may be transmitted separately from, or together with, the information on the application of operation 301, or may be included in the information on the application. The server 108 may receive account information, identify at least one account included in the account information, and identify the genetic information of the specific user corresponding to at least one account. The server 108 may determine at least one genetic element of operation 303 from genetic information corresponding to at least one account.

FIG. 4 illustrates an example of an operation of an electronic device for identifying a genetic element corresponding to an attribute of application from genetic information stored in the electronic device according to various embodiments. Operations exemplified in a flowchart 400 of FIG. 4 may be performed by the electronic device 101 of FIG. 1 or by the processor 120 of the electronic device 101.

Operations 401 to 403 of FIG. 4 may be related to the operation 203 of FIG. 2.

Referring to FIG. 4, in operation 401, the processor 120 may identify an attribute related to user's genetic information for an application. In other words, the processor 120 may identify an attribute of application. For another example, the processor 120 may identify an application category. For example, the processor 120 may identify the attribute of application and/or the application category, based on an application ID of the application. In various embodiments, the user's genetic information may be stored in the memory 130. In this case, the processor 120 may identify the attribute of application and/or the application category to identify at least one genetic element corresponding to the attribute of application and/or the application category from the genetic information.

In operation 403, the processor 120 may identify at least one genetic element corresponding to the attribute from the genetic information stored in the electronic device 101. In other words, the processor 120 may identify at least one genetic element corresponding to the attribute of application and/or the application category from the user's genetic information stored in the memory 130. For example, the processor 120 may determine at least one genetic element corresponding to the attribute of application and/or the application category from the genetic information, based on a genetic information mapping table.

In various embodiments, the processor 120 may control the communication module 190 to receive genetic information from the server 108, and may store the received genetic information in the memory 130. To this end, the processor 120 may control the communication module 190 to transmit to the server 108 a message for a genetic information request. The message for the genetic information request may include information on at least one user account configured in the electronic device 101. In this case, the server 108 which has received the message for the genetic information request may identify genetic information of the user corresponding to the account based on received at least one account, and may transmit the identified genetic information to the electronic device 101.

In various embodiments, the genetic information mapping table may be stored in advance in the memory 130 of the electronic device 101.

In various embodiments, the processor 120 may control the communication module 190 to receive the genetic information mapping table from the server 108.

Hereinafter, an operation for considering user's feedback information when changing a setting value will be described in greater detail with reference to FIG. 5.

Figure 5:
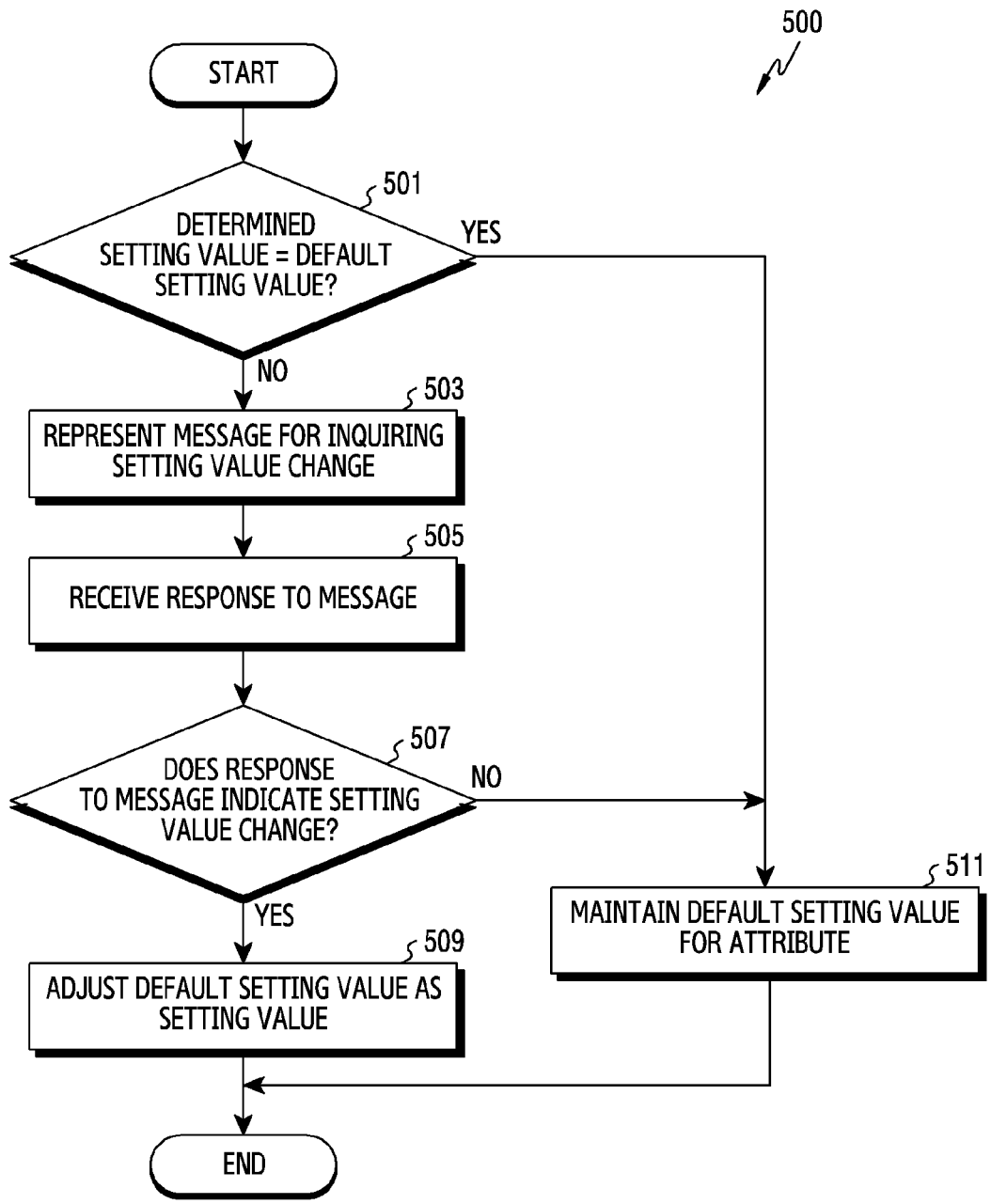
FIG. 5 illustrates an example of an operation of an electronic device for determining a setting value based on a feedback for a setting value change according to various embodiments.

FIG. 5 illustrates an example of an operation of an electronic device for determining a setting value based on a feedback for a setting value change according to various embodiments. Operations exemplified in a flowchart 500 of FIG. 5 may be performed by the electronic device 101 of FIG. 1 or by the processor 120 of the electronic device 101.

Operations 501 to 511 of FIG. 5 may be related to the operation 205 of FIG. 2.

Referring to FIG. 5, in operation 501, the processor 120 may determine whether a determined setting value (e.g., a current setting value) is equal to a default setting value. In other words, the processor 120 may determine a setting value for an attribute of application based on at least one genetic element corresponding to the attribute of application, and may compare the determined setting value with the default setting value. In various embodiments, the default setting value may be a value configured irrespective of a user's genetic element or may be a value configured without considering the user's genetic element. In various embodiments, the processor 120 may determine that the current setting value is equal to the default setting value even if the current setting value is within a specific margin of error from the default setting value. Further, the processor 120 may compare the current setting value with a pre-set value or an old setting value instead of the default setting value. If the current setting value is equal to the default setting value, the processor 120 may perform operation 511. Otherwise, if the current setting value is different from the default setting value, the processor 120 may perform operation 503.

In operation 503, the processor 120 may represent a message for inquiring a setting value change. If the current setting value is different from the default setting value, the processor 120 may determine that the setting value change is required, and may represent the message for inquiring the setting value change. For example, the processor 120 may display the message for inquiring the setting value change via the display unit 160, or may output the message for inquiring the setting value change as a voice signal via the audio module 170.

In operation 505, the processor 120 may receive a response to the message. For example, the processor 120 may receive a user's touch input corresponding to the response to the message via a touch circuit of the display unit 160. For another example, the processor 120 may receive a user's voice input corresponding to the response to the message via a microphone of the input unit 150. In various embodiments, the response to the message may include an approval of the setting value change or a rejection of the setting value change.

In operation 507, the processor 120 may determine whether the response to the message indicates the setting value change. For example, if the response to the message includes the approval of the setting value change, the processor 120 may determine that the response to the message indicates the setting value change. For another example, if the response to the message includes the rejection of the setting value change, the processor 120 may determine that the response to the message indicates to maintain the setting value. If the response to the message indicates the setting value change, the processor 120 may perform operation 509. Otherwise, if the response to the message does not indicate the setting value change (i.e., if the response to the message includes the rejection of the setting value change), the processor 120 may perform operation 511.

In operation 509, the processor 120 may adjust the default setting value as the current setting value. For another example, the processor 120 may adjust a pre-set value and/or an old setting value as the current setting value. The processor 120 may provide a service customized to the user and/or a service individualized to the user by adjusting the default setting value as a setting value in which a user's genetic characteristic is reflected.

In operation 511, the processor 120 may maintain the default setting value for the attribute. For example, if the default setting value is equal to the current setting value the processor 120 may determine that the default setting value properly reflects the user's genetic characteristic, and may maintain the default setting value for the attribute of application. For another example, if the response to the message indicates to maintain the setting value (i.e., if the response to the message includes the rejection of the setting value change), the processor 120 may recognize that the user intends to use the default setting value irrespective of the genetic element, and may maintain the default setting value for the attribute of application.

In various embodiments, operations 503 to 507 may be referred to as a 'feedback procedure', and the feedback procedure may be omitted. In other words, the processor 120 may not perform the feedback procedure, and may adjust the default setting value to the current setting value if the current setting value is different from the default setting value, and may maintain the default setting value for the attribute of application if the current setting value is equal to the default setting value. In this case, the operations 503 to 507 may be omitted.

In various embodiments, the message for inquiring the setting value change may include a user's condition information related to the genetic element. In various embodiments, the user's condition information related to the genetic element is a genetic trait expressed by the genetic element, and may include, for example, at least one of color blindness, race, gender, height, hair color, eye color (e.g., iris color), skin color, contour, heart condition, caffeine sensitivity, and flat foot. For example, if the user has blue iris color, the message for inquiring the setting value change may be represented such as 'The user's iris color is blue. Do you want to change the setting value for the configuration of the IR sensor to match blue eye?'.

In various embodiments, if the response to the message indicates to maintain the setting value (i.e., if the response to the message includes the rejection of the setting value change), the processor 120 may control the communication module 190 to transmit information on a genetic element related to the maintaining of the setting value to the server 108. In other words, when the user's condition information corresponding to the genetic element is considered, if the response to the message indicates to maintain the setting value although the setting value change is recommended, the processor 120 may control the communication module 190 to transmit the information on the genetic element related to the maintaining of the setting value to the server 108. The server 108 may receive the information on the genetic element related to the maintaining of the setting value, and may utilize this information as statistical data for determining the user's condition information. Further, the server 108 may update the user's condition information related to the genetic element, based on statistical information. In other words, the information on the genetic element related to the maintaining of the setting value may be used when the server 108 updates the user's condition information related to the genetic element.

Figure 6:
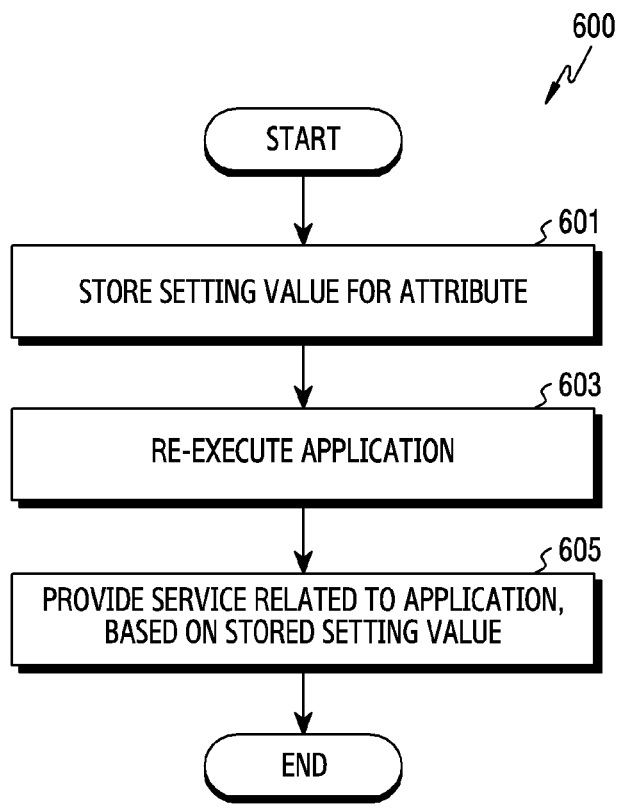
FIG. 6 illustrates an example of an operation of an electronic device for storing a setting value in which a user's genetic characteristic is reflected and for utilizing the stored setting value according to various embodiments.

FIG. 6 illustrates an example of an operation of an electronic device for storing a setting value in which a user's genetic characteristic is reflected and for utilizing the stored setting value according to various embodiments. Operations exemplified in a flowchart 600 of FIG. 6 may be performed by the electronic device 101 of FIG. 1 or by the processor 120 of the electronic device 101.

Referring to FIG. 6, in operation 601, the processor 120 may store a setting value for an attribute of application in the memory 130. The processor 120 may identify at least one genetic element corresponding to the attribute of application, and may determine the setting value for the attribute of application based on the at least one genetic element and then store the determined setting value.

In operation 603, the processor 120 may re-execute the application. The processor 120 may store a setting value determined while executing the application, and may re-execute the application after the application ends.

In operation 605, the processor 120 may provide a service related to the application based on the stored setting value. In other words, the processor 120 may provide the service related to the application based on the stored setting value without identifying the at least one genetic element in response to the re-execution of the application. Accordingly, the processor 120 may provide the application service based on an optimal setting value more rapidly and effectively by skipping a procedure of determining the setting value when the application is re-executed, without having to determine the setting value whenever the application s executed.

Hereinafter, examples for determining a setting value according to a specific genetic element will be described in detail with reference to FIG. 7 to FIG. 11.

Figure 7:
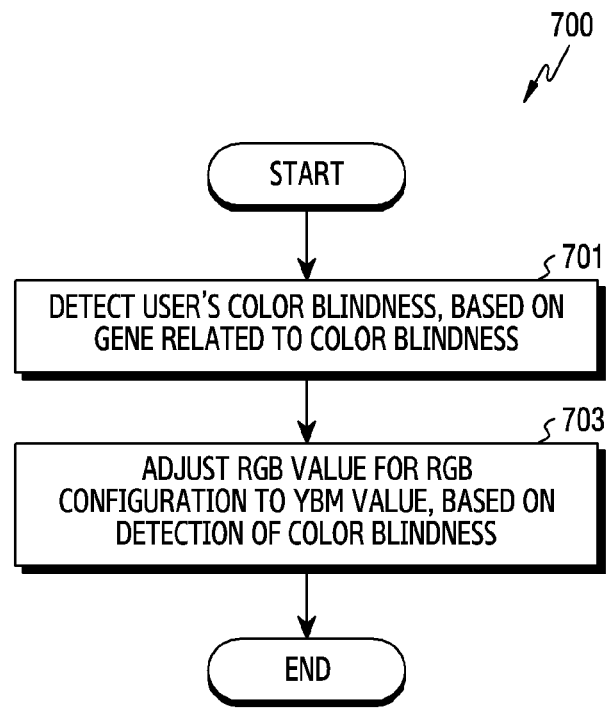
FIG. 7 illustrates an operation of an electronic device for determining a setting value of a Red, Blue, Green (RGB) configuration for image data according to various embodiments.

FIG. 7 illustrates an operation of an electronic device for determining a setting value of an RGB configuration for image data according to various embodiments. Operations exemplified in a flowchart 700 of FIG. 7 may be performed by the electronic device 101 of FIG. 1 or by the processor 120 of the electronic device 101.

Operations 701 to 703 of FIG. 7 may be related to the operation 205 of FIG. 2.

Referring to FIG. 7, in operation 701, the processor 120 may detect color blindness of a user, based on a gene related to the color blindness. For example, congenital color blindness may occur when there is a mutation in genes of CNGA3, CNGB3, GNAT2, OPN1LW, OPN1MW, and OPN1SW. The processor 120 may identify a mutation in a gene related to the color blindness, and may determine the user's color blindness based on the mutation.

In operation 703, the processor 120 may adjust an RGB value of image data to a YBM value based on detecting of the color blindness. For example, the processor 120 may adjust the setting value such that an element representing red expresses yellow, an element representing green expresses blue, and an element representing blue expresses blue in a display such as an LCD or OLED display.

In various embodiments, the processor 120 may adjust a setting value for an RGB configuration in an application for which the display unit 160 is used or usable.

In various embodiments, the processor 120 may control the display unit 160 to display image data by using the YBM value adjusted according to the gene related to the color blindness.

In various embodiments, the processor 120 may perform a feedback procedure for adjusting the setting value for the RGB configuration. For example, the processor 120 may represent a message for inquiring a setting value change (i.e., from the RGB value to the YBM value), and may receive a response to the message. If the response to the message indicates to change to the YBM value, the processor 120 may adjust the RGB value of the image data to the YBM value.

Figure 8:
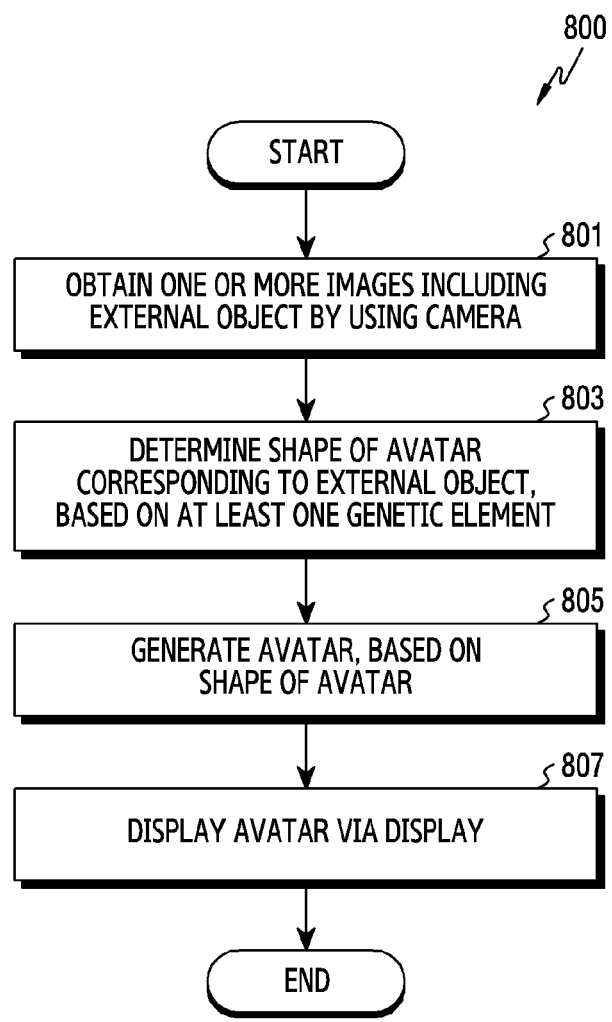
FIG. 8 illustrates an example of an operation of an electronic device for determining a shape of an avatar based on a genetic element according to various embodiments.

FIG. 8 illustrates an example of an operation of an electronic device for determining a shape of an avatar based on a genetic element according to various embodiments. Operations exemplified in a flowchart 800 of FIG. 8 may be performed by the electronic device 101 of FIG. 1 or by the processor 120 of the electronic device 101.

Operations 801 to 807 of FIG. 8 may be related to the operation 207 of FIG. 2.

Referring to FIG. 8, in operation 801, the processor 120 may obtain one or more images including an external object by using a camera the camera module 180). The external object may include at least part of a user's face. The processor 120 may track a change in the external object by using the camera module 180, and may obtain one or more images captured by the camera module 180 during the tracking.

In operation 803, the processor 120 may determine a shape of an avatar corresponding to the external object based on at least one genetic element. In various embodiments, the at least one genetic element used to determine the shape of the avatar may include at least one of a gene related to a user's race, a gene related to a user's gender, a gene related to a user's height, a gene related to user's hair color, a gene related to user's eye color, a gene related to user's skin color, and a gene related to a user's contour. The processor 120 may determine a detailed shape of the avatar corresponding to the genetic element. For example, the processor 120 may determine a setting value related to a race of the avatar based on the gene related to the user's race, and may determine a setting value related to a gender of the avatar based on the gene related to the user's gender.

In operation 805, the processor 120 may create the avatar based on the determined shape of the avatar. The processor 120 may combine individual elements of the avatar determined based on the user's genetic element, and may create the avatar in which the user's genetic characteristic is reflected.

In operation 807, the processor 120 may display the avatar via a display (e.g., the display unit 160). In other words, the processor 120 may control the display unit 160 to display the avatar in which the user's genetic characteristic is reflected, thereby providing more improved user experience.

When only a capture image for the user is used without considering the user's genetic element to create the avatar, features (e.g., race, skin tone, hair color, eye color) related to an actual user's shape cannot be reflected in the avatar, and information on an image captured by a camera (e.g., the camera module 180) cannot accurately reflect the user's actual shape due to a variety of environment variables (e.g., day/night, whether the user wears makeup, whether the user wears color lenses, user's height, weight, restriction in capturing). As a result, a distorted avatar may be created.

Therefore, if the user's genetic information is utilized when the avatar is created, the created avatar may be more similar to the shape of the user.

In various embodiments, an example of a genetic element (or a gene) used to determine the shape of the avatar, a feature of the genetic element (i.e., a genetic trait expressed by the gene and a setting value for the shape of the avatar may be represented by Table 3 below.

TABLE 3

| Feature | Gene | Feature | Setting value for shape of avatar |
|---|---|---|---|
| Race | FTO, NCTB | 70% Asian, 20% European, 10% African | Setting value for race of avatar, setting value for ratio of race |
| Height | CNA | Tall, medium, or short height | Setting value for height of avatar |
| Eye color | ABC | Brown, blue, or green | Setting value for eye color of avatar |
| Skin color | DCG | Black, yellow, or white | Setting value for skin color of avatar |
| Hair type | Frizzled | Whether hair is curly | Setting value for hair type of avatar |
| ... | ... | ... | ... |

In various embodiments, the processor 120 may use at least part of information shown in Table 3 above to determine a setting value for the shape of the avatar and create the avatar by applying the setting value.

In various embodiments, the processor 120 may perform a feedback procedure to determine the setting value for the shape of the avatar. For example, the processor 120 may represent a message for inquiring a setting value change (i.e., a setting value change for a detailed shape of the avatar) and receive a response to the message. If the response to the message indicates to adjust the shape of the avatar by reflecting a genetic element, the processor 120 may adjust a setting value for the avatar shape.

Figure 9:
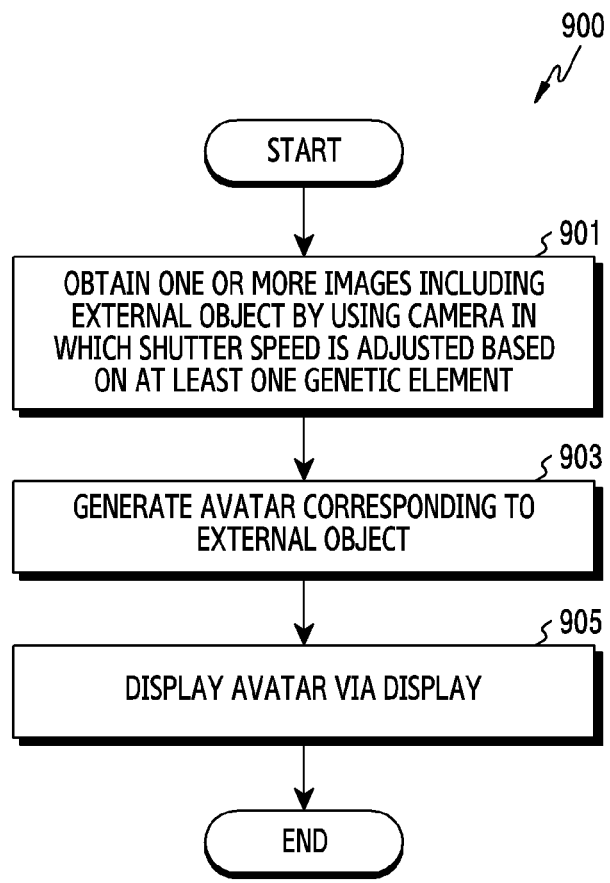
FIG. 9 illustrates an example of an operation of an electronic device for creating an avatar by controlling a camera configuration based on a genetic element according to various embodiments.

FIG. 9 illustrates an example of an operation of an electronic device for creating an avatar by controlling a camera configuration based on a genetic element according to various embodiments. Operations exemplified in a flowchart 900 of FIG. 9 may be performed by the electronic device 101 of FIG. 1 or by the processor 120 of the electronic device 101.

Operations 901 to 905 of FIG. 9 may be related to the operation 207 of FIG. 2.

Referring to FIG. 9, in operation 901, the processor 120 may obtain one or more images including an external object by using a camera (e.g., the camera module 180) in which a shutter speed is adjusted based on at least one genetic element. In various embodiments, a setting value for a camera configuration of the camera module 180 may include at least one of the shutter speed and an exposure time. The processor 120 may adjust the shutter speed of the camera module 180 based on at least one genetic element, acid may obtain one or more images including the external object by using the adjusted camera module 180. For example, if user's skin color identified according to the genetic element has a dark tone, the processor 120 may adjust the shutter speed of the camera module 180 to be slow so that a camera lens can absorb a great amount of light to the maximum extent possible. In various embodiments, at least one genetic element may include at least one of a gene related to a user's race, a gene related to a user's gender, a gene related to user's height, a gene related to user's hair color, a gene related to user's eye color, a gene related to user's skin color, and a gene related to a user's contour. The external object may include at least part of the user's face. The processor 120 may track a change in the external object by using the camera module 180, and may obtain one or more images captured by the camera module 180 during the tracking.

In operation 903, the processor 120 may create an avatar corresponding to the external object. The external object may properly reflect a user's genetic characteristic according to the camera configuration adjusted when the image is obtained. Therefore, the processor 120 may create the avatar in which the user's genetic characteristic is reflected.

In operation 905, the processor 120 may display the avatar via a display (e.g., the display unit 160). In other words, the processor 120 may control the display unit 160 to display the avatar in which the user's genetic characteristic is reflected, thereby providing more improved user experience.

In various embodiments, even if the avatar is created by using an image obtained via a camera in which a camera configuration is adjusted according to a genetic element, similarly to the operation 803, the processor 120 may determine the shape of the avatar corresponding to the external object from the obtained image, based on at least one genetic element. In other words, the processor 120 may further consider the user's genetic element one more time in the process of determining the avatar shape.

In various embodiments, the processor 120 may perform a feedback procedure to determine the setting value for the camera configuration. For example, the processor 120 may represent a message for inquiring a setting value change (i.e., an adjustment of a shutter speed of a camera) and receive a response to the message. If the response to the message indicates to adjust the shutter speed of the camera by reflecting a genetic element, the processor 120 may adjust the shutter speed of the camera to be slow.

The genetic information may provide information related to various features, such as race, gender, height, hair color, eye color, skin tone, and contour, used to create the avatar in a scientific manner. When the genetic information is used to reflect a user's innate attribute in addition to a capture image for the user in order to create the avatar, a more individualized avatar may be created. In various embodiments, the processor 120 may utilize genetic information of a growing child to simulate how a height, skin tone/color, and weight of the child will change, and may utilize genetic information of a grown adult to simulate an aging process in terms of skin wrinkles, pigmentation, elasticity, and hair loss. Through the aforementioned simulations, the processor 120 may predict user's condition information based on a genetic attribute of the user, and may prevent and take measure against factors which are not desired by the user.

Figure 10:
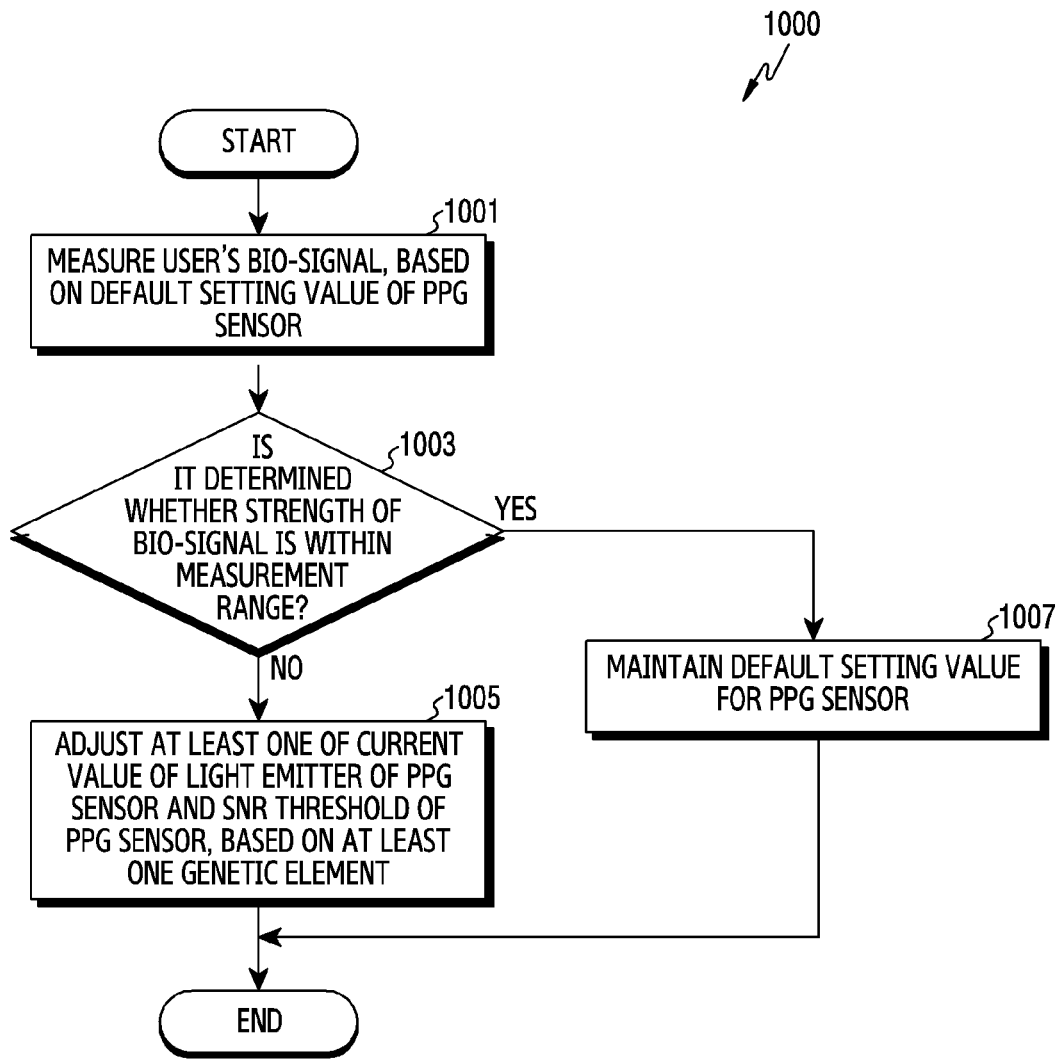
FIG. 10 illustrates an operation of an electronic device for determining a setting value for a configuration of a PhotoPlethysmoGraphy (PPG) sensor based on a genetic element according to various embodiments.

FIG. 10 illustrates an operation of an electronic device for determining a setting value for a configuration of a PPG sensor based on a genetic element according to various embodiments. Operations exemplified in a flowchart 1000 of FIG. 10 may be performed by the electronic device 101 of FIG. 1 or by the processor 120 of the electronic device 101.

Operations 1001 to 1007 of FIG. 10 may be related to the operation 205 of FIG. 2.

Referring to FIG. 10, in operation 1101, the processor 120 may measure a bio-signal of the user, based on a default setting value of a PPG sensor. In various embodiments, the bio-signal may include a signal emitted from a light emitter of the PPG sensor, absorbed and/or reflected on user's skin, and received in a light receiver of the PPG sensor. The processor 120 may measure a signal bio-signal) received in the light receiver of the PPG sensor. For example, the processor 120 may measure strength of the signal received in the light receiver of the PPG sensor. In various embodiments, the default setting value of the PPG sensor may include at least one of a default current value of the light emitter of the PPG sensor and a default Signal to Noise Ratio (SNR) threshold of the PPG sensor. In various embodiments, the processor 120 may use a pre-set value or an old setting value instead of the default setting value of the PPG sensor, in order to measure the bio-signal of the user.

In operation 1003, the processor 120 may determine whether strength of the bio-signal is within a measurement range. In various embodiments, the measurement range is configured in advance, or is configurable according to a user's input. The measurement range may include a range of bio-signal strength allowed to obtain reasonable heartbeat information. If the strength of the bio-signal is out of the measurement range, the processor 120 may perform operation 1005. Otherwise, if the strength of the bio-signal is within the measurement range, the processor 120 may perform operation 1007.

In operation 1005, the processor 120 may adjust at least one of a current value of the light emitter of the PPG sensor and an SNR threshold of the PPG sensor, based on at least one genetic element. In various embodiments, the at least one genetic element may include a gene related to user's skin color and a gene related to a user's heart condition. A ratio at which a signal emitted from the light emitter of the PPG sensor is absorbed in skin may vary depending on at least one of user's skin color, a skin expression status, a characteristic of skin expression, and a skin thickness. For example, a ratio (i.e., absorption ratio) at which the signal emitted from the light emitter of the PPG sensor is absorbed in skin may increase in proportion to darkness of skin color. Since an amount of photons received in the light emitter decreases in proportion to the absorption ratio, a heartbeat may be measured relatively incorrectly. Accordingly, based on at least one genetic element indicating that user's skin color is dark, the processor 120 may increase a current value of the light emitter of the PPG sensor and/or increase an SNR threshold of the PPG sensor so that the light receiver of the PPG sensor more properly recognizes the photons. On the other hand, the absorption ratio may decrease when the skin color is bright, and an amount of photons received in the light receiver increases. As a result, measured current may be saturated with the same current value. Accordingly, based on at least one genetic element indicating that user's skin color is bright, the processor 120 may decrease the current value of the light emitter and/or decrease the SNR threshold of the PPG sensor so that the light receiver of the PPG sensor does not recognize an unnecessarily great amount of photons. For another example, based on at least one genetic element indicating that a user's heartbeat is weak, the processor 120 may increase the current value of the light emitter of the PPG sensor and/or increase the SNR threshold of the PPG sensor so that the light receiver of the PPG sensor more properly recognizes the photons. Further, the processor 120 may represent a message indicating to increase wearable tightness of a heartbeat measurement device (e.g., a wearable sensor). As such, the processor 120 may accurately detect heartbeat information also for a variety of skin color, by adjusting the current value and/or SNR threshold of the light emitter of the PPG sensor.

In operation 1007, the processor 120 may maintain the default setting value for the PPG sensor. In other words, if the strength of the bio-signal is within the measurement range, the processor 120 may maintain the default setting value for the PPG sensor.

In various embodiments, the processor 120 may measure the heartbeat information, based on a setting value adjusted for the configuration of the PPG sensor.

In various embodiments, the processor 120 may adjust the setting value for the configuration of the PPG sensor, without having to determine whether the strength of the bio-signal is within the measurement range. In other words, the processor 120 determines the setting value for the configuration of the PPG sensor based on at least one genetic element, without having to determine whether the strength of the bio-signal is within the measurement range. If the determined setting value is equal to the default setting value, the default setting value may be maintained. Otherwise, if the determined setting value is different from the default setting value, the default setting value may be adjusted to the determined setting value. For this adjustment, the feedback procedure of FIG. 5 may be used. In this case, operations 1001, 1003, and 1007 may be omitted.

Figure 11:
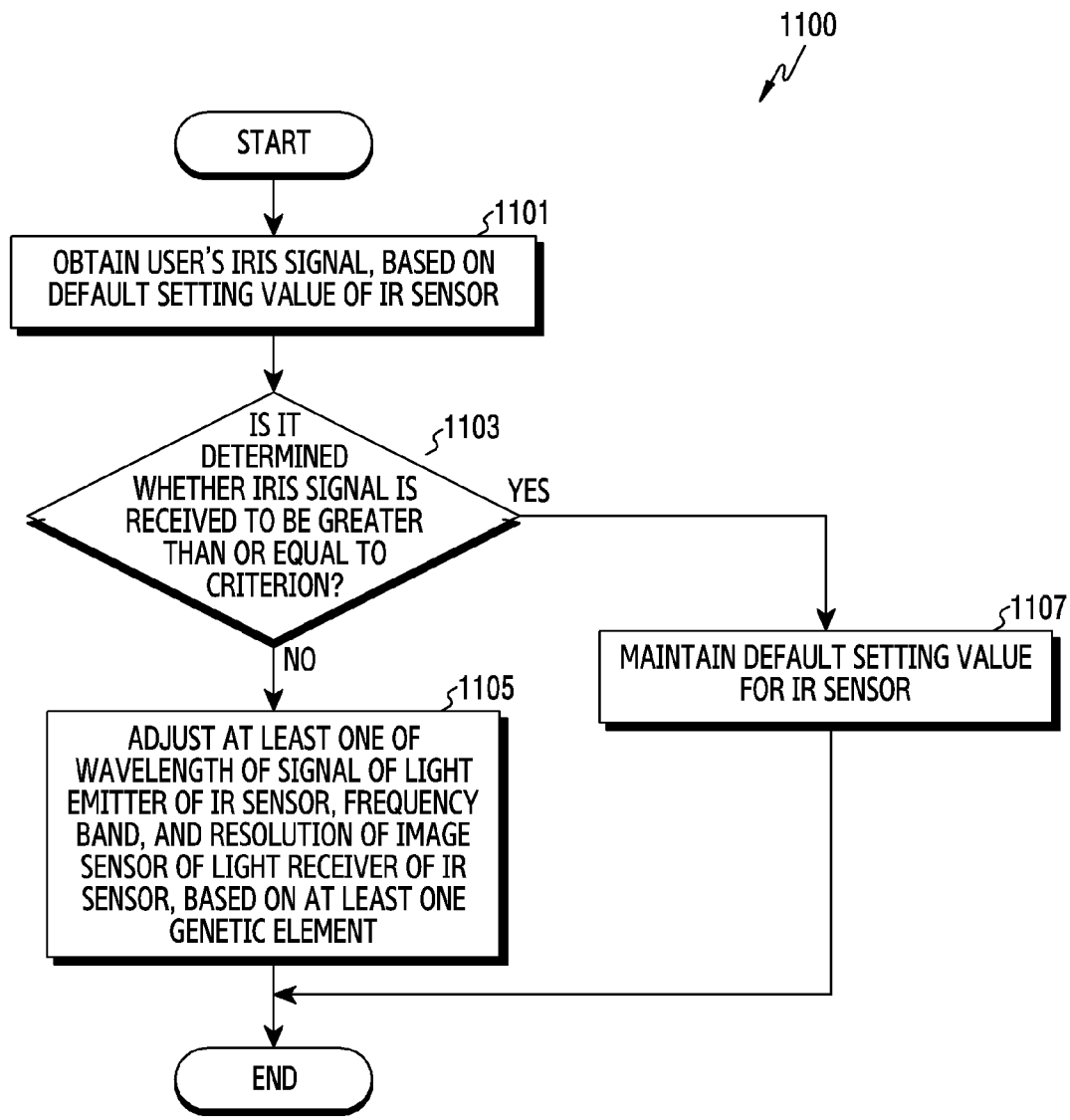
FIG. 11 illustrates an operation of an electronic device for determining a setting value for a configuration of an Infra-Red (IR) sensor based on a genetic element according to various embodiments.

FIG. 11 illustrates an operation of an electronic device for determining a setting value for a configuration of an IR sensor based on a genetic element according to various embodiments. Operations exemplified in a flowchart 1100 of FIG. 11 may be performed by the electronic device 101 of FIG. 1 or by the processor 120 of the electronic device 101.

Operations 1101 to 1107 of FIG. 11 may be related to the operation 205 of FIG. 2.

Referring to FIG. 11, in operation 1101, the processor 120 may obtain an iris signal of a user, based on a default setting value of an IR sensor. In various embodiments, the iris signal of the user may include user's iris information, and the iris information may include information on user's iris color. The iris color may include at least one of hue, intensity, and saturation of the iris. A signal emitted from a light emitter of the IR sensor may be received in a light receiver by being partially absorbed by a pattern of the iris and partially reflected. The processor 120 may obtain the user's iris information by analyzing a signal received in the light receiver of the IR sensor. The iris color may be represented variously by a pigment layer inside the iris, and may be different for each race and/or individual. In addition, the iris color may be different for each eye of the same person, and may vary depending on a location even in one eye. For example, the iris color may be represented by brown, hazel, amber, green, gray, blue, purple, and/or red. Since a signal is received differently in the light receiver of the IR sensor according to each color, the processor 120 may obtain the user's iris information by analyzing the signal received in the light receiver of the IR sensor. In various embodiments, the default setting value of the IR sensor may include at least one of a wavelength (or a frequency band) of a signal to be emitted from the IR sensor or to be absorbed by the IR sensor and a resolution of an image sensor of the light emitter. In various embodiments, in order to obtain the user's iris information, the processor 120 may use a pre-set value or an old setting value instead of the default setting value.

In operation 1103, the processor 120 may determine whether the iris signal is received to be greater than or equal to criterion. In various embodiments, the iris signal may include a signal emitted from a light emitter of the IR sensor, absorbed and/or reflected on user's pupil, and received in a light receiver of the IR sensor. In addition, in various embodiments, a criterion to be compared with the iris signal may include standard brightness for iris color. If the iris signal is not received to be greater than or equal to the criterion if the iris signal is received to be less than the criterion), the processor 120 may perform operation 1105.

Otherwise, if the iris signal is received to be greater than or equal to the criterion, the processor 120 may perform operation 1107.

In operation 1105, the processor 120 may adjust at least one of a wavelength (or a frequency band) of a signal of a light emitter of the IR sensor and a resolution of an image sensor of a light receiver of the fit sensor, based on at least one genetic element. In various embodiments, the at least one genetic element may include a gene related to user's iris color. The user's iris color is a user's genetic characteristic expressed by two or more genes having effect on each other, and may determine iris color represented with expressions of brown, green, and blue respectively by genes of EYCL1, EYCL2, and EYCL3. Since an amount of a signal received in the light receiver of the IR sensor decreases in proportion to darkness of the iris color, the iris may be recognized relatively incorrectly. On the other hand, since the amount of the signal received in the light receiver of the IR sensor increases in proportion to brightness of the iris color, current measured in the light receiver is saturated with the same current value, and thus the iris may be recognized relatively incorrectly. Accordingly, if the iris signal is not received to be greater than or equal to the criterion, based on at least one genetic element, the processor 120 may adjust at least one of a wavelength (or a frequency band) of a signal of a light emitter (or a signal of a light receiver) of the IR sensor and a resolution of an image sensor of the light receiver of the IR sensor. As such, the processor 120 may detect iris information accurately also for a variety of iris color by adjusting at least one of the wavelength (or the frequency band) of the signal of the light emitter (or the signal of the light receiver) of the IR sensor and the resolution of the image sensor of the light emitter of the IR sensor.

In operation 1107, the processor 120 may maintain a default setting value for the IR sensor. In other words, if the iris color is received to be greater than or equal to standard brightness for iris color, the processor 120 may maintain the default setting value for the IR sensor.

In various embodiments, the processor 120 may measure the iris information, based on a setting value adjusted for the configuration of the IR sensor.

In various embodiments, the processor 120 may adjust the setting value for the configuration of the IR sensor based on at least one genetic element representing user's race and/or an external environment element. For example, the external environment element may include intensity of ambient light for the IR sensor. If the intensity of the ambient light is strong, iris recognition may be incorrectly performed, and since recognition of the IR sensor and iris color may be influenced by user's race, the processor 120 may adjust the setting value for the configuration of the IR sensor based on the at least one genetic element representing the user's race and/or the external environment element.

In various embodiments, the processor 120 may adjust the setting value for the configuration of the IR sensor, without having to determine whether the iris signal is received to be greater than or equal to the criterion. In other words, the processor 120 may determine the setting value for the configuration of the IR sensor based on the at least one genetic element without having to determine whether the iris signal is received to be greater than or equal to the criterion. If the determined setting value is equal to the default setting value, the default setting value may be maintained. Otherwise, if the determined setting value is different from the default setting value, the default setting value may be adjusted to the determined setting value. For this adjustment, the feedback procedure of FIG. 5 may be used. In this case, operations 1101, 1103, and 1107 may be omitted.

A method of operating an electronic device (e.g., the electronic device 101) according to various embodiments described above may include identifying at least one genetic element corresponding to an attribute related to genetic information of a user with respect to the application, determining a setting value for the attribute, based on the at least one genetic element, and providing a service related to the application, based on the determined setting value.

In various embodiments, the identifying of the at least one genetic element may include transmitting, to a server, information on the application, and receiving, from the server, information including the at least one genetic element determined based on the information on the application.

In various embodiments, the identifying of the at least one genetic element may include identifying an attribute related to user's genetic information for the application, and identifying the at least one genetic element corresponding to the attribute from the genetic information stored in the electronic device.

In various embodiments, the at least one genetic element corresponding to the attribute may be determined based on a table representing a mapping relation between attributes related to a plurality of applications and genetic elements of the genetic information.

In various embodiments, the determining of the setting value may include comparing the setting value with a default setting value, representing a message for inquiring a setting value change if the setting value is different from the default setting value as a result of the comparison, receiving a response to the message, and adjusting the default setting value to the setting value if the response to the message indicates the setting value change.

In various embodiments, the determining of the setting value may include maintaining the default setting value for the attribute if the response to the message indicates to maintain the setting value, and transmitting information on a genetic element related to the maintaining of the setting value to a server. The information on the genetic element may be used to update user's condition information related to the genetic element.

In various embodiments, the method may include storing the setting value for the attribute, and providing the service related to the application based on the stored setting value without identifying the at least one genetic element in response to re-execution of the application.

In various embodiments, the at least one genetic element may include a gene related to color blindness, and the attribute includes a Red, Blue, Green (RGB) configuration for image data. The determining of the setting value may include detecting the color blindness of the user based on the gene related to the color blindness, and adjusting an RGB value for the RGB configuration to a Yellow, Blue, Maintained (YBM) value, based on the detection of the color blindness. The providing of the service may include displaying the image data, based on the YBM value.

In various embodiments, the at least one genetic element may include at least one of a gene related to a race of the user, a gene related to a gender of the user, a gene related to a height of the user, a gene related to hair color of the user, a gene related to eye color of the user, a gene related to skin color of the user, and a gene related to a contour of the user. The attribute may include a shape of an avatar. The providing of the service may include obtaining one or more images including an external object by using a camera, determining the shape of the avatar corresponding to the external object, based on the at least one genetic element, creating the avatar, based on the shape of the avatar, and displaying the avatar via a display.

In various embodiments, the at least one genetic element may include at least one of a gene related to a race of the user, a gene related to hair color of the user, a gene related to eye color of the user, and a gene related to skin color of the user. The attribute may include a camera configuration. The providing of the service may include obtaining one or more images including an external object by using a camera of which a shutter speed is adjusted based on the at least one genetic element, creating an avatar corresponding to the external object, and displaying the avatar via a display.

In various embodiments, the at least one genetic element may include at least one of a gene related to skin color of the user and a gene related to a heart condition of the user. The attribute may include a configuration for a PhotoPlethysmoGraphy (PPG) sensor. The determining of the setting value may include measuring a bio-signal of the user, based on a default setting value of the PPG sensor, determining whether an intensity of the bio-signal is within a measurement range, and if the intensity of the bio-signal is out of the measurement range, adjusting at least one of a current value of a light emitter of the PPG sensor and a Signal to Noise Ratio (SNR) threshold of the PPG sensor, based on the at least one genetic element.

In various embodiments, the at least one genetic element may include a gene related to iris color of the user. The attribute may include a configuration for an Infra-Red (IR) sensor. The determining of the setting value may include obtaining an iris signal of the user, based on a default setting value of the IR sensor, determining whether the iris signal is received to be greater than or equal to a criterion, and if the iris signal is not received to be greater than or equal to the criterion, adjusting at least one of a wavelength of a signal of a light emitter of the IR sensor, a frequency band of a signal of the light emitter, and a resolution of an image sensor of a light receiver of the IR sensor.

Methods based on the embodiments disclosed in the claims and/or specification of the disclosure can be implemented in hardware, software, or a combination of both.

When implemented in software, computer readable recording medium for storing one or more programs (i.e., software modules) can be provided. The one or more programs stored in the computer readable recording medium are configured for execution performed by one or more processors in the electronic device. The one or more programs include instructions for allowing the electronic device to execute the methods based on the embodiments disclosed in the claims and/or specification of the disclosure.

The program (i.e., the software module or software) can be stored in a random access memory, a non-volatile memory including a flash memory, a Read Only, Memory (ROM), an Electrically Erasable Programmable Read Only Memory (EEPROM), a magnetic disc storage device, a Compact Disc-ROM (CD-ROM), Digital Versatile Discs (DVDs) or other forms of optical storage devices, and a magnetic cassette. Alternatively, the program can be stored in a memory configured in combination of all or some of these storage media. In addition, the configured memory can be plural in number.

Further, the program can be stored in an attachable storage device capable of accessing the electronic device through a communication network such as the Internet, an Intranet, a Local Area Network (LAN), a Wide LAN (WLAN), or a Storage Area Network (SAN) or a communication network configured by combining the networks. The storage device can have an access to a device for performing an embodiment of the disclosure via an external port. In addition, an additional storage device on a communication network can have an access to the device for performing the embodiment of the disclosure.

In the aforementioned specific embodiments of the disclosure, a component: included in the disclosure is expressed in a singular or plural form according to the specific example embodiment proposed herein. However, the singular or plural expression is selected properly for a situation proposed for the convenience of explanation, and thus the disclosure is not limited to a single or a plurality of components. Therefore, a component expressed in a plural form can also be expressed in a singular form, or vice versa.

While the disclosure has been shown and described with reference to certain embodiments thereof, it will be understood by those skilled in the art that various changes in form and details may be made therein without departing from the spirit and scope of the disclosure as defined by the appended claims. Therefore, the scope of the disclosure is defined not by the detailed description thereof but by the appended claims, and all differences within equivalents of the scope will be construed as being included in the disclosure.

Although the present disclosure has been described with various embodiments, various changes and modifications may be suggested to one skilled in the art. It is intended that the present disclosure encompass such changes and modifications as fall within the scope of the appended claims.

What is claimed is:

1. A method of operating an electronic device, the method comprising:
    executing an application;
    identifying at least one genetic element corresponding to an attribute related to genetic information of a user with respect to the application;
    determining a setting value for the attribute based on the at least one genetic element;
    comparing the setting value with a default setting value;
    if the setting value is within a specific margin of error from the default setting value, maintaining the default setting value for the attribute;
    if the setting value is out of from the specific margin of error from the default setting value, outputting a message for inquiring a setting value change;
    receiving a response to the message;
    adjusting the default setting value to the setting value based on the response to the message indicating the setting value change; and
    providing a service related to the application based on the adjusted default setting value,
    wherein the default setting value includes at least one of a pre-set value or a previous setting value, and
    wherein the response to the message includes an approval of the setting value change or a rejection of the setting value change.

2. The method of claim 1, wherein the identifying of the at least one genetic element comprises:
    transmitting, to a server, information on the application; and
    receiving, from the server, information comprising the at least one genetic element determined based on the information on the application.

3. The method of claim 1, wherein the identifying of the at least one genetic element comprises:
    identifying the attribute related to the genetic information of the user for the application; and identifying the at least one genetic element corresponding to the attribute from the genetic information stored in the electronic device.

4. The method of claim 1, wherein the at least one genetic element corresponding to the attribute is determined based on a table representing a mapping relation between attributes related to a plurality of applications and genetic elements of the genetic information.

5. The method of claim 1, wherein the determining of the setting value comprises:
transmitting information on a genetic element of the at least one genetic element related to the maintaining of the setting value to a server,
wherein the information on the genetic element is used to update condition information of the user related to the genetic element.

6. The method of claim 1, further comprising:
storing the setting value for the attribute; and
providing the service related to the application based on the stored setting value without identifying the at least one genetic element in response to re-execution of the application.

7. The method of claim 1, wherein:
the at least one genetic element comprises a gene related to color blindness,
the attribute comprises a Red, Green, Blue (RGB) configuration for image data,
the determining of the setting value comprises:
detecting the color blindness of the user based on the gene related to the color blindness; and
adjusting an RGB value for the RGB configuration to a Yellow, Blue, Maintained (YBM) value based on the detection of the color blindness, and
the providing of the service comprises displaying the image data based on the YBM value.

8. The method of claim 1, wherein:
the at least one genetic element comprises at least one of a gene related to a race of the user, a gene related to a gender of the user, a gene related to a height of the user, a gene related to hair color of the user, a gene related to eye color of the user, a gene related to skin color of the user, or a gene related to a contour of the user,
the attribute comprises a shape of an avatar, and
the providing of the service comprises:
obtaining one or more images comprising an external object by using a camera;
determining the shape of the avatar corresponding to the external object based on the at least one genetic element;
creating the avatar based on the shape of the avatar; and
displaying the avatar via a display.

9. The method of claim 1, wherein:
the at least one genetic element comprises at least one of a gene related to a race of the user, a gene related to hair color of the user, a gene related to eye color of the user, or a gene related to skin color of the user,
the attribute comprises a camera configuration, and
the providing of the service comprises:
obtaining one or more images comprising an external object by using a camera of which a shutter speed is adjusted based on the at least one genetic element;
creating an avatar corresponding to the external object; and
displaying the avatar via a display.

10. The method of claim 1, wherein:
the at least one genetic element comprises at least one of a gene related to skin color of the user or a gene related to a heart condition of the user,
the attribute comprises a configuration for a PhotoPlethysmoGraphy (PPG) sensor, and
the determining of the setting value comprises:
measuring a bio-signal of the user based on a default setting value of the PPG sensor;
determining whether an intensity of the bio-signal is within a measurement range; and
based on the intensity of the bio-signal not being within the measurement range, adjusting at least one of a current value of a light emitter of the PPG sensor or a Signal to Noise Ratio (SNR) threshold of the PPG sensor based on the at least one genetic element.

11. The method of claim 1, wherein:
the at least one genetic element comprises a gene related to iris color of the user,
the attribute comprises a configuration for an Infra-Red (IR) sensor, and
the determining of the setting value comprises:
obtaining an iris signal of the user based on a default setting value of the IR sensor;
determining whether the iris signal is received to be greater than or equal to a criterion; and
based on the iris signal not being received to be greater than or equal to the criterion, adjusting at least one of a wavelength of a signal of a light emitter of the IR sensor, a frequency band of a signal of the light emitter, or a resolution of an image sensor of a light receiver of the IR sensor.

12. An electronic device comprising:
a camera;
a display;
a sensor;
a memory;
a transceiver; and
a processor configured to:
execute an application;
identify at least one genetic element corresponding to an attribute related to genetic information of a user with respect to the application;
determine a setting value for the attribute based on the at least one genetic element;
compare the setting value with a default setting value;
if the setting value setting is within a specific margin of error from the default setting value, maintain the default setting value for the attribute;
if the setting value is out of from the specific margin of error from the default setting value, output a message for inquiring a setting value change;
receive a response to the message;
adjust the default setting value to the setting value based on the response to the message indicating the setting value change; and
provide a service related to the application based on the adjusted default setting value,
wherein a default setting value includes at least one of a pre-set value or a previous setting value, and
wherein the response to the message includes an approval of the setting value change or a rejection of the setting value change.

13. The device of claim 12, wherein the processor is configured to:
   transmit, to a server, information on the application by controlling the transceiver; and
   receive, from the server, information comprising the at least one genetic element determined based on the information on the application by controlling the transceiver.

14. The device of claim 12, wherein the processor is configured to:
   identify the attribute related to genetic information of the user for the application; and
   identify the at least one genetic element corresponding to the attribute from the genetic information stored in the electronic device.

15. The device of claim 12, wherein the at least one genetic element corresponding to the attribute is determined based on a table representing a mapping relation between attributes related to a plurality of applications and genetic elements of the genetic information.

16. The device of claim 12, wherein the processor is configured to:
   transmit information on a genetic element of the at least one genetic element related to the maintaining of the setting value to a server by controlling the transceiver,
   wherein the information on the genetic element is used to update user's condition information related to the genetic element.

17. The device of claim 12, wherein the processor is configured to:
   store the setting value for the attribute in the memory; and
   provide the service related to the application based on the stored setting value without identifying the at least one genetic element in response to re-execution of the application.

18. The device of claim 12, wherein:
   the at least one genetic element comprises a gene related to color blindness,
   the attribute comprises a Red, Green, Blue (RGB) configuration for image data, and
   the processor is configured to:
      detect the color blindness of the user based on the gene related to the color blindness;
      adjust an RGB value for the RGB configuration to a Yellow, Blue, Maintained (YBM) value based on the detection of the color blindness; and
      display the image data based on the YBM value.

19. The device of claim 12, wherein:
   the at least one genetic element comprises at least one of a gene related to a race of the user, a gene related to a gender of the user, a gene related to a height of the user, a gene related to hair color of the user, a gene related to eye color of the user, a gene related to skin color of the user, or a gene related to a contour of the user,
   the attribute comprises a shape of an avatar, and
   the processor is configured to:
      obtain one or more images comprising an external object by using a camera;
      determine the shape of the avatar corresponding to the external object, based on the at least one genetic element;
      create the avatar based on the shape of the avatar; and
      display the avatar via the display.

20. The device of claim 12, wherein:
   the at least one genetic element comprises at least one of a gene related to a race of the user, a gene related to hair color of the user, a gene related to eye color of the user, or a gene related to skin color of the user,
   the attribute comprises a camera configuration, and
   the processor is configured to:
      obtain one or more images comprising an external object by using a camera of which a shutter speed is adjusted based on the at least one genetic element;
      create an avatar corresponding to the external object; and
      display the avatar via the display.

21. The device of claim 12, wherein:
   the at least one genetic element comprises at least one of a gene related to skin color of the user or a gene related to a heart condition of the user,
   the attribute comprises a configuration for a PhotoPlethysmoGraphy (PPG) sensor, and
   the processor is configured to:
      measure a bio-signal of the user based on a default setting value of the PPG sensor;
      determine whether an intensity of the bio-signal is within a measurement range; and
      based on the intensity of the bio-signal not being within the measurement range, adjust at least one of a current value of a light emitter of the PPG sensor or a Signal to Noise Ratio (SNR) threshold of the PPG sensor based on the at least one genetic element.

22. The device of claim 12, wherein:
   the at least one genetic element comprises a gene related to iris color of the user,
   the attribute comprises a configuration for an Infra-Red (IR) sensor, and
   the processor is configured to:
      obtain an iris signal of the user based on a default setting value of the IR sensor;
      determine whether the iris signal is received to be greater than or equal to a criterion; and
      based on the iris signal not being received to be greater than or equal to the criterion, adjust at least one of a wavelength of a signal of a light emitter of the IR sensor, a frequency band of a signal of the light emitter, or a resolution of an image sensor of a light receiver of the IR sensor.

* * * * *